United States Patent [19]

Nwaonicha et al.

[11] Patent Number: 5,434,307
[45] Date of Patent: Jul. 18, 1995

[54] SYNTHESIS OF 12-OXODODECANOIC ACID OXIME FROM VERNOLIC ACID

[75] Inventors: Chukwuma P. Nwaonicha, Adelphi; Folahan O. Ayorinde, Kettering, both of Md.

[73] Assignee: Howard University, Washington, D.C.

[21] Appl. No.: 65,333

[22] Filed: May 21, 1993

[51] Int. Cl.[6] .................. C07C 249/04; C07C 251/32
[52] U.S. Cl. ................................ 564/259; 564/262; 564/268; 562/623
[58] Field of Search ............... 562/623; 564/259, 262, 564/268

[56] References Cited

FOREIGN PATENT DOCUMENTS

| 1574471 | 7/1969 | France . |
| 2207699 | 7/1972 | Germany . |
| 3010673 | 3/1980 | Germany . |
| 60-58083 | 4/1985 | Japan . |
| 60-163849 | 8/1985 | Japan . |
| 1283796 | 8/1972 | United Kingdom . |

OTHER PUBLICATIONS

Industrial and Engineering Chemistry, vol. 62, No. 3, (1970) Wolfgang Griehl et al., pp. 16–22: *Nylon-12—Preparation.*
Lipids, vol. 23, No. 4 (1988), Henry Rakoff, pp. 280–284: *Preparation of Methyl cis-9, cis-12, cis-15-Octadecatrienoate-15,16-$d_2$ and Methyl cis-9,cis-12,cis-15-Octadecatrienoate-6,6,7,7-$d_4$.*

Primary Examiner—José G. Dees
Assistant Examiner—Dwayne C. Jones
Attorney, Agent, or Firm—Kenyon & Kenyon

[57] ABSTRACT

A process for producing 12-oxododecanoic acid oxime, a novel compound which can be used as a raw material in several industrial processes, is disclosed. The disclosed process relies on a renewable raw material, vernolic (cis-12,13-epoxy-cis-9-octadecenoic) acid. The process utilizes readily available chemical technology which does not involve the use of gaseous hydrocarbon or petrochemical-base feedstock. Hydrogenation of vernolic acid produces 12,13-epoxystearic acid, which can be oxidized with periodic acid to give 12-oxododecanoic acid, which can be reacted with hydroxylamine to yield 12-oxododecanoic acid oxime. A process for reducing the 12-oxododecanoic acid oxime to yield 12-aminododecanoic acid, the monomer for nylon-12, is also disclosed.

9 Claims, 1 Drawing Sheet

FIGURE 1: A Preferred Synthesis of Nylon-12 from Purified Vernolic Acid
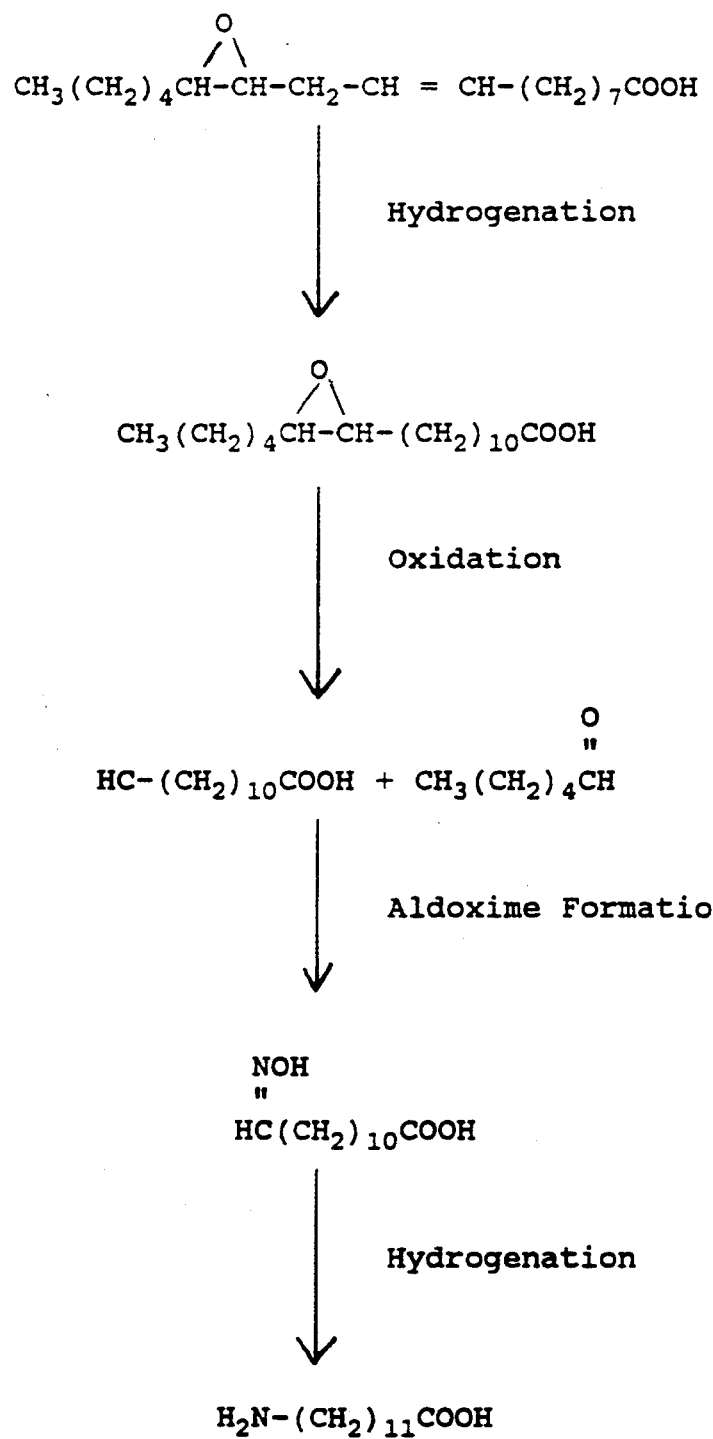

SYNTHESIS OF 12-OXODODECANOIC ACID OXIME FROM VERNOLIC ACID

FIELD OF THE INVENTION

This invention relates to the synthesis of 12-oxododecanoic acid oxime, a novel aldoxime, which can be used as the starting material for the production of several important monomers. More specifically, this invention relates to a process by which vernolic acid (cis 12,13-epoxy-cis-9-octadecenoic) is transformed into 12-oxododecanoic acid oxime, which can be further transformed into 12-aminododecanoic acid, the monomer for Nylon-12.

BACKGROUND OF THE INVENTION

The novel aldoxime of the present invention has been found to be an important industrial intermediate which can be easily converted to several important monomers. For example, by hydrogenation, the novel aldoxime can be converted into 12-aminododecanoic acid, the monomer for Nylon-12. Nylon-12 is an engineering polyamide fiber having a myriad of uses. It is often used as a curing agent for epoxy resins, a modifier for polyester materials, or by the automobile industry for the preparation of oil and gasoline resistant tubes. Nylon-12 can be used in hydraulic systems, electrical cables, metal coatings, ship propellers, screws, injection syringes, sterilized films and bags for medical purposes and foodstuffs, e.g., the skin for sausages. The properties of Nylon-12 can be readily modified by adding to it polyamide additives, including plasticizers, pigments and heat and light stabilizers.

Presently, 12-aminododecanoic acid is produced by a process involving the initial trimerization of butadiene to give cyclododecatriene. Presently, the butadiene is produced from petroleum products—either from catalytic dehydrogenation of petroleum gases, i.e., butene or a butene-butane mixture, or by cracking naphtha ($C_6H_{14}$—$C_7H_{16}$) or light oil. Butadiene is then hydrogenated to cylododecane, which, in turn, is oxidized to give cylododecanol. The cylododecanol is oxidized to the corresponding ketone, then to an insoluble oxime, which gives lauryl lactam through a Beckmann rearrangement. Lauryl lactam is subsequently converted to Nylon-12 via the intermediate, 12-aminododecanoic acid.

According to the present invention, commercially important chemicals, heretofore derived from petrochemical feedstocks, are, instead, synthesized from a renewable raw material. In the present invention, a novel compound, 12-oxododecanoic acid oxime, which can easily be converted into the monomer of Nylon-12, is synthesized from vernolic acid, a naturally epoxidized C-18 fatty acid, obtained from the seed oil of *Vernonia galamensis*. The seed of *Vernonia galamensis*, an annual herb, indigenous to tropical and sub-tropical Africa, contains about 40% naturally epoxidized triglyceride oil. Upon saponification and acidification, the seed oil yields about 75–80% vernolic acid, 10–13% linoleic acid, 4–6% oleic acid, and 3–6% saturated acids, making it an abundant source of a unique and naturally epoxidized fatty acid.

Vernonia oil has been the subject of several recent studies. In one study, vernonia oil was reacted with acetic acid. By cleavage of the epoxy group, hydroxy acetate was formed, which was then saponified and methylated to obtain methyl 12,13-dihydroxyoleate. This intermediate then was oxidized with periodic acid to give methyl 12-oxo-cis-9-dodecenoate. In the present invention, a process for the direct oxidation of the epoxy group of vernolic acid, to form an oxo acid is provided. This oxo acid is a key intermediate which is subsequently converted to 12-oxododecanoic acid oxime, which can then be converted to any one of several commercial products, including, for example, 12-aminododecanoic acid.

BRIEF DESCRIPTION OF THE DRAWINGS

FIG. 1 shows a reaction scheme for the synthesis of Nylon-12 from Vernolic acid according to the present invention.

SUMMARY OF THE INVENTION

Vernolia oil undergoes saponification and acification followed by cold temperature (−20° C.) crystallization to yield a methylated product comprised of vernolic, palmitic, oleic, linoleic and stearic acid. The vernolic acid is isolated and further purified through a series of low temperature recrystalizations. The purified vernolic acid,

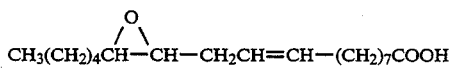

is then hydrogenated to yield 12,13-epoxystearic acid, having the formula:

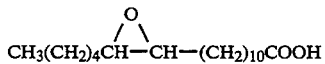

The 12,13-epoxystearic acid is then oxidized to yield 12-oxododecanoic acid,

By reacting the 12-oxododecanoic acid with hydroxylamine, 12-oxododecanoic acid oxime

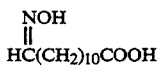

is formed. The Nylon-12 monomer, 12-aminododecanoic acid:

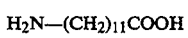

is synthesized from the aldoxime acid via a hydrogenation reaction.

DETAILED DESCRIPTION OF THE INVENTION

Upon saponification and acidification, crude *Vernonia galamensis* oil usually contains about 75–80% vernolic acid. Any of the well-known isolation and purification techniques, (i.e., extraction, chromatography, cold temperature crystallization) may be used to isolate and purify the epoxy acid. Cold temperature crystallization was used since it utilizes the least amount of solvent and is the most efficient and cost effective technique.

For the transformation of vernolic acid to 12-aminododecanoic acid, the inventors prefer the following sequence of reactions: hydrogenation of the olefinic group, oxidation of the epoxy group, aldoxime formation and hydrogenation of the aldoxime acid. However, the present invention is not limited by this sequence, since it is possible to oxidize the epoxy group prior to hydrogenation of the olefinic group. Such oxidation could be effected by first opening up the epoxy functionality to form a diol, and then oxidizing the diol to afford the oxo acid.

A more complete description and understanding of the present invention is provided below through a set of preferred steps for carrying out the present invention.

Saponification And Acidification Of Vernonia Oil

Methanol (50 mL) and 4.97 g (0.124 mol) sodium hydroxide were added to a 250 mL distilling flask, equipped with a magnetic stir bar. The flask was then equipped with a condenser, and the mixture heated to reflux until complete dissolution of the sodium hydroxide. In one portion 5.12 g ($5.5 \times 10^{-3}$ mol) vernonia oil was added to the hot alkaline solution. The resulting brownish solution was refluxed with continuous stirring for ten minutes, then immediately transferred into a beaker, and allowed to form a semi-solid on cooling. Approximately 100 g ice were added to the beaker, mixed thoroughly, and followed by addition of 100 mL water with mixing. The cold mixture was vacuum-filtered which produced an off-white solid soap in the filter bed. The soap was transferred into a beaker, and mixed with approximately 100 g ice, and 100 mL water, then acidified with approximately 4 mL acetic acid. The acidified mixture was immediately vacuum-filtered, producing a white solid (containing mixture of acids). The cold white solid was transferred into a beaker containing 100 mL hexane, with mixing to dissolve the acid, and the resulting mixture transferred into a separatory funnel. The hexane layer was stripped to (4.5 g) resulting in crude vernolic acid. Gas chromatographic/mass spectrometric analysis of the methylated crude product re-indicated the presence of several acids—palmitic, oleic, linoleic, stearic and vernolic.

Purification Of Vernolic Acid

The vernolic acid isolated above was 76% pure based on the oxirane value of 4.1%. Purification of the acid was accomplished by low temperature recrystallizations. Hexane (50 mL) was added to 4.5 g of the crude vernolic acid in a 150 mL beaker and placed in a $-20°$ C. freezer for 24 hours. The resulting solid was vacuum-filtered and rinsed with an additional 50 mL ice-cold hexane to give 2.77 g (56.72% yield) vernolic acid (m.p. 23°–25° C. lit. m.p. 25°–28° C., oxirane % 5.22, 97.0% purity).

Hydrogenation Of Vernolic Acid

A 2.6 g ($8.8 \times 10^{-3}$ mol) sample of vernolic acid was placed in a paar hydrogenation bottle, followed by 0.03 grams ($1.3 \times 10^{-4}$ mol) platinum oxide (Adam's catalyst) and 15 mL of methanol. The bottle and its contents were fitted to a paar high-pressure system. The air in the bottle was evacuated with a water aspirator after which it was filled with hydrogen gas to maintain a pressure of 3 atm for 45 minutes with continuous shaking. After hydrogenation, methanol (15 mL) was added to the reaction mixture, then heated to gentle boiling to dissolve the product. The hot mixture was quickly filtered to remove the suspension of black platinum and the filtrate evaporated to give 2.42 g (93% yield) of white solid, consisting of 99% (GC purity) 12,13-epoxystearic acid after recrystallization in hexane (m.p. 52°–54° C., Lit. m.p. 52°–53.5° C.).

The IR spectrum of both 12,13-epoxystearic acid and vernolic acid showed strong absorption at 1700 cm$^{-1}$ (Carbonyl) 824 cm$^{-1}$ and 846 cm$^{-1}$ (epoxy group). The absorption at 1600 cm$^{-1}$ on the spectrum of vernolic acid correspond to the olefinic protons. The p-nmr spectrum of vernolic acid and 12,13-epoxystearic acid were closely related except that the absorption due to the olefinic protons at 5.5 ppm was absent in the 12,13-epoxystearic acid spectrum. The epoxy protons at 2.9 ppm was present in both spectra. Carbon-13 nmr (proton decoupled) of vernolic acid indicated the presence of carbonyl carbon at 180 ppm, olefinic carbons at 124 ppm and 133 ppm, the carbons attached to the epoxy functionality appeared at 56 ppm and 57 ppm. On the other hand, a comparison of the carbon-13 spectrum of 12,13-epoxystearic acid revealed the absence of olefinic carbon. Another significant difference in the spectrum is the single peak at 57 ppm (epoxy carbons), suggesting that the two carbons on the epoxy functionality of the 12,13-epoxystearic acid are chemically identical.

This preferred hydrogenation step was found to be quantitative. However, in order to avoid formation of hydroxy acids, presumably due to catalytic opening of the epoxy functionality, reaction time should not exceed one hour. Since the hydrogenation reaction can be catalyzed by any of a wide range of catalysts, and the hydrogenation of the trans-isomer of vernolic acid yields the same product, catalysts other than platinum oxide may be successfully utilized.

Oxidation Of 12,13-epoxystearic Acid

A 2.40 g (0.008 mol) sample of the acid was placed in a 250 mL Erlenmeyer flask and dissolved with 18 mL water and 9 mL tertiary butyl alcohol. The mixture was stirred continuously for homogeneity, followed by addition of 1.95 g (0.0086 mol) periodic acid in one portion. The reaction mixture was then stirred for 5 hours, after which 150 mL ice-cold water was added. The mixture was stirred for another 30 minutes and the resulting solid was vacuum-filtered to give crude 12-oxododecanoic acid. The acid was washed, then recrystallized with light petroleum (bp 35°–60° C.) to give 1.22 g 12-oxododecanoic acid (73% yield, m.p. 53°–54° C.) and hexanal. There was no attempt to isolate the hexanal.

In the carbon-13 nmr spectrum of 12-oxododecanoic acid, two distinct peaks were observed at 180 ppm (carbonyl carbon of the carboxylic acid) and 203 ppm (carbonyl carbon of the aldehyde). The mass spectra data of the 12-oxododecanoic acid indicated extensive fragmentations with a base peak at m/z 74 due to Mclafferty rearrangement, a peak at m/z 229 represents M+1 ion. Other diagnostic ions were m/z 210 (M—H$_2$O), m/z 200 (M—CO), m/z 179 (M—OCH$_3$) and m/z 185 (M—CH$_2$OH). The 12-oxododecanoic acid showed an infrared absorption at 2850 cm$^{-1}$ and 3500 cm$^{-1}$ that are characteristic of aldehyde and acid respectively. The carbonyl absorption was observed at 1705 cm$^{-1}$. The p-nmr data indicated the presence of proton attached to the carbonyl group at 9.3 ppm. The multiplets at 1.8–0.8 ppm and 2.5–2.22 ppm were due to the methylene protons.

A reaction time of five hours appears to optimize the oxidation to 12-oxododecanoic acid. When the reaction was allowed to proceed for more than five hours, some dodecanedioic acid and hexanoic acid were produced, apparantly as a result of over oxidation of the aldehydes. Conversely, when the reaction proceeded for less than five hours, the reaction was incomplete and unreacted epoxy acid remained.

While the preferred reaction step provides for the one step oxidation of the epoxy functionality, cleavage of the epoxy fuctionality could be stepwise. For instance, there can be an initial opening of the epoxy functionality to form a diol, which is subsequently oxidized to the oxo product. It is well known that iodates cleave vicinal diols to form oxo products.

Preparation Of 12-oxododecanoic Acid Oxime

A 2.75 g (0.04 mol) sample of hydroxylamine hydrochloride was placed in a 250 mL Erlenmeyer flask, followed by addition of 16.5 mL of water, gently warming the content of the flask. To the flask were added 11 mL of 10% sodium hydroxide, and 1.1 g (0.005 mol) of 12-oxododecanoic acid. Ethanol (15 mL) was added to give a clear solution. The mixture was warmed on a water bath for 10 minutes after which it was cooled in an ice-bath. The resulting solid was filtered and dried to give 1.05 g (93% yield) of aldoxime acid. Recrystallization was carried out in water/ethanol mixture (4:1) to give 0.92 g (80% yield) pure aldoxime acid (m.p. 104°–106° C.). Elemental Analysis found: C, 62.65; H, 9.92; N, 5.72%. Calculated for $C_{12}H_{23}NO_3$: C, 62.85; H, 10.11; N, 6.11%.

The infrared spectrum of the aldoxime acid showed a carbon-nitrogen double bond (C=N) at 1690 cm$^{-1}$ and carbonyl (C=O) at 1700 cm$^{-1}$. The O—H stretching vibration of both functional groups were observed at the 2950 cm$^{-1}$–3300 cm$^{-1}$ region. Delineation of the syn/anti isomeric composition of the aldoxime was accomplished with carbon-13 nmr studies. Quantitative carbon-13 nmr spectrum showed three absorption peaks due to sp$^2$-hybridized carbons. The signal at 178.018 ppm was attributed to the carbon of the carbonyl group, while the signals at 153.011 ppm and 152.462 ppm were assigned to the carbons of the anti- and syn-aldoxime groups respectively. Thus, carbon-13 and GC/MS analysis indicated a ratio of syn/anti isomers to be about 7:3.

The MS of both syn and anti isomers gave similar fragmentation patterns except that the syn isomer showed a base peak at m/z 74 and no molecular ion peak was observed due to loss of OH to give the ion at m/z 226. On the other hand, the anti isomer showed a base peak at m/z 59 that may be attributed to a Mclafferty type rearrangement involving the oxime part of the molecule. An M+1 peak was apparent at m/z 244 for the anti isomer.

The present invention encompasses the conversion of the 12-oxododecanoic acid to its oxime using mildly acidic conditions. However, steps should be taken not to reduce the effectiveness of the nucleophilic agent, thereby preventing the formation of the oxime. In the preferred reaction step, the conversion was undertaken in an acidic medium (pH 4–5) using hydroxylamine hydrochloride, since a lower pH would reduce the nucleophilicity of the hydroxylamine.

Preparation Of 12-aminododecanoic Acid

In a paar hydrogenation bottle was placed 0.92 g ($4\times10^{-3}$ mol) 12-oxododecanoic acid oxime, 10 mL methanol, and then 0.005 g ($2.2\times10^{-5}$ mol) platinum oxide (Adam's catalyst). The bottle was fitted to a paar high-pressure system, deaerated, then filled with hydrogen gas to maintain a pressure of about 3 atm for 1.5 hours with continuous shaking. After hydrogenation, 10 mL of methanol was added to the reaction mixture, then heated to gentle boiling to dissolve the product. The hot mixture was quickly filtered to remove suspension of black platinum, after which the filtrate on evaporation gave 0.85 g (92% yield) 12-aminododecanoic acid. Recrystallization was effected with ethanol/water mixture (1:1) to give 0.80 g (87% yield) 12-aminododecanoic acid (m.p. 184°–186° C, Lit. 185°–187° C.).

The GC of the 12-aminododecanoic acid showed two peaks when methylated with diazomethane. The peaks correspond to primary amino ester $H_2N(CH_2)_{11}CO_2CH_3$ and tertiary amino ester $(CH_3)_2N(CH_2)_{11}CO_2CH_3$. The diagnostic ions observed in the mass spectra data of the primary amino ester are M+1 ion at m/z 230, m/z 30 (base peak), m/z 156 (M-$CH_2)_6CO_2CH_3$). The tertiary amino ester gave molecular ion peak at m/z 257 and a base peak at m/z 44. Other fragmentation ions were m/z 58 [(CH$_3$)$_2$—N—CH$_2$]$^+$, m/z 170 (M-87) and m/z 212 (M-45).

The IR of the 12-aminododecanoic acid exhibit an absorption at 1646 cm$^{-1}$ due to the C=O and at 2900–3200 cm$^{-1}$ region due to the O—H group. The usual —NH$_2$ group absorption at 3300 cm$^{-1}$ was partially overlapped by the strong O—H absorption of the carboxylic acid group at this region. However, the —NH$_2$ bending frequency was observed at 1508 cm$^{-1}$ and C—N stretching bond produced a strong peak at 1400 cm$^{-1}$.

The processes described above could easily be adapted to use the alkyl esters of the appropriate fatty acids, and that minor variations in the processes involving different solvent systems, temperature, oxidizing agent, hydrogenation catalyst are possible, hence the present invention is not limited to the use of specific oxidizing agent, solvent systems or temperature variations as outlined above. For example, the processes for the production of 12-oxododecanoic acid oxime described above can be effected by starting with methyl-(alkyl)vernolate:

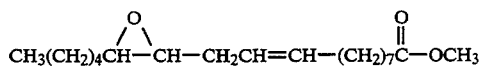

to give alkyl 12-oxododecanoate oxime:

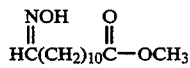

which, upon hydrolysis, would yield the desired 12-oxododecanoic acid oxime. Alternatively, the alkyl 12-oxododecaanoate oxime could be hydrogenated to give alkyl 12-aminododecanoate:

which could subsequently be hydrolyzed to yield 12-aminododecanoic acid:

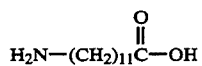

Consequently, we intend only to be limited by the following claims.

We claim:

1. A process for making 12-oxododecanoic acid oxime comprising:
   (a) cleaving the epoxy functionality from vernolic acid via a one-step oxidation process; and
   (b) reacting the resulting product with hydroxylamine.

2. The process of claim 1 which further comprises the hydrogenation of the vernolic acid prior to the cleaving of the epoxy functionality.

3. A process for making 12-oxododecanoic acid oxime comprising:
   (a) hydrogenation of vernolic acid to form 12,13epoxystearic acid;
   (b) oxidation of the 12,13-epoxystearic acid to form 12-oxododecanoic acid; and
   (c) reacting the 12-oxododecanoic acid with hydroxylamine to form the 12-oxododecanoic acid oxime.

4. A process for making 12-oxododecanoic acid from vernolic acid comprising cleavage of the C12–C13 bond by a one-step oxidation of the epoxy functionality.

5. The process of claim 4 which further comprises the hydrogenation of the vernolic acid prior to the cleaving of the epoxy functionality.

6. A process for making 12-oxododecanoic acid oxime comprising:
   (a) oxidation of the 12,13-epoxystearic acid to form 12-oxododecanoic acid; and
   (b) reacting the 12-oxododecanoic acid with hydroxylamine to form the 12-oxododecanoic acid oxime.

7. A process for making 12-oxododecanoic acid oxime comprising reacting 12-oxododecanoic acid with hydroxylamine.

8. A process for making 12-oxododecanoic acid oxime comprising:
   (a) hydrogenation of methyl (alkyl) vernolate to form an intermediate product;
   (b) oxidation of the intermediate product to form alkyl 12-oxododecanoate oxime; and
   (c) hydrolysis of the alkyl 12-oxododecanoate oxime.

9. The process according to any of the above claims in which an alkyl ester of the acid is used in place of the acid.

* * * * *